(12) United States Patent
Nelson et al.

(10) Patent No.: US 10,470,908 B2
(45) Date of Patent: Nov. 12, 2019

(54) AUTOMATIC-SEALING BALLOON-FILLING CATHETER SYSTEM

(71) Applicant: Allurion Technologies, Inc., Natick, MA (US)

(72) Inventors: David W. Nelson, Wayland, MA (US); Matthew J. Lapinski, Andover, MA (US); Bruce A. Horwitz, Newton, MA (US); Samuel Moss, Brookline, MA (US)

(73) Assignee: Allurion Technologies, Inc., Natick, MA (US)

( * ) Notice: Subject to any disclaimer, the term of this patent is extended or adjusted under 35 U.S.C. 154(b) by 0 days.

(21) Appl. No.: 16/286,321

(22) Filed: Feb. 26, 2019

(65) Prior Publication Data

US 2019/0262157 A1    Aug. 29, 2019

Related U.S. Application Data

(60) Provisional application No. 62/635,272, filed on Feb. 26, 2018.

(51) Int. Cl.
*A61F 5/00*    (2006.01)

(52) U.S. Cl.
CPC ............ *A61F 5/0043* (2013.01); *A61F 5/003* (2013.01); *A61F 5/0089* (2013.01)

(58) Field of Classification Search
CPC .................. A61F 5/003; A61F 5/0089; A61M 25/010185; A61M 25/10185
See application file for complete search history.

(56) References Cited

U.S. PATENT DOCUMENTS

| | | |
|---|---|---|
| 5,507,808 A | 4/1996 | Becker |
| 6,162,251 A | 12/2000 | Kredovski |
| 8,784,486 B2 | 7/2014 | Schuessler |
| 9,463,106 B2 | 10/2016 | Khieu et al. |
| 9,827,128 B2 | 11/2017 | Brister et al. |
| 2003/0229384 A1 | 12/2003 | Mon |
| 2010/0114311 A1 | 5/2010 | Becker |
| 2014/0188151 A1 | 7/2014 | Gaur et al. |
| 2014/0296903 A1 | 10/2014 | Gaur et al. |
| 2017/0312111 A1 | 11/2017 | Sharma et al. |

FOREIGN PATENT DOCUMENTS

| | | |
|---|---|---|
| CA | 2925648 | 5/2007 |
| WO | WO 2009/059803 | 5/2009 |

*Primary Examiner* — Richard G Louis
(74) *Attorney, Agent, or Firm* — Levine Bagade Han LLP

(57) ABSTRACT

Valve assemblies for use with expandable devices that are positioned within remote cavities and more particularly relates to the catheters/conduits used to inflate these devices with fluid.

28 Claims, 19 Drawing Sheets

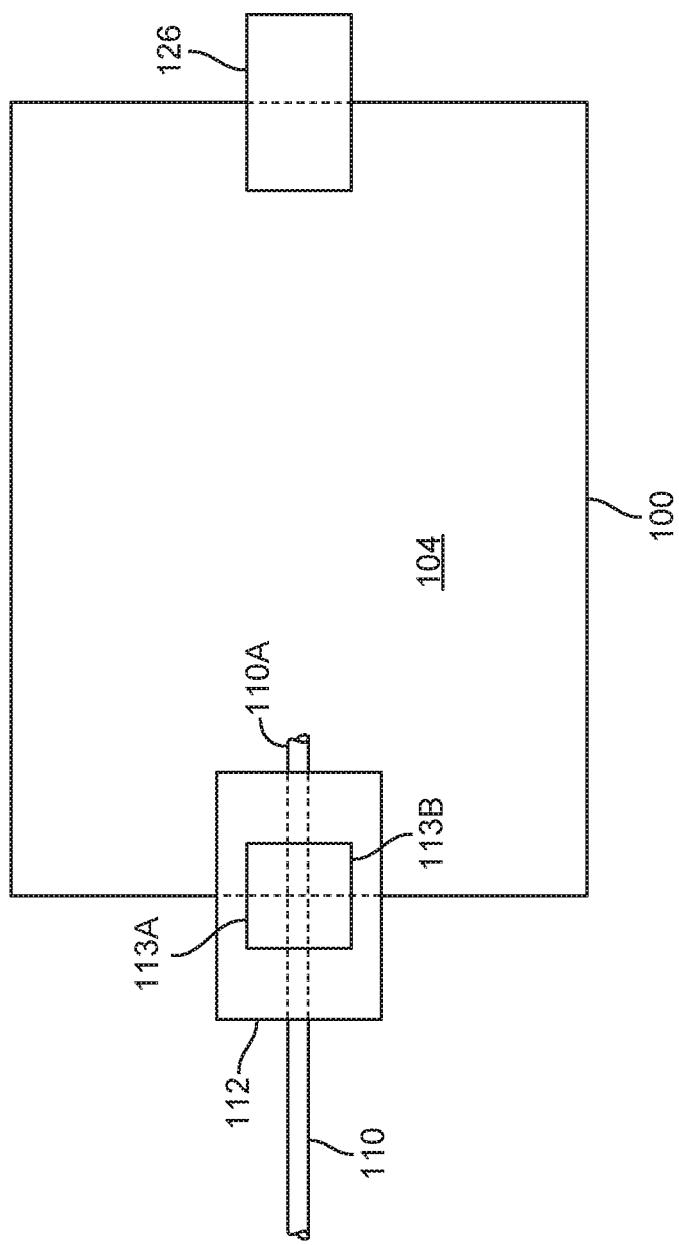

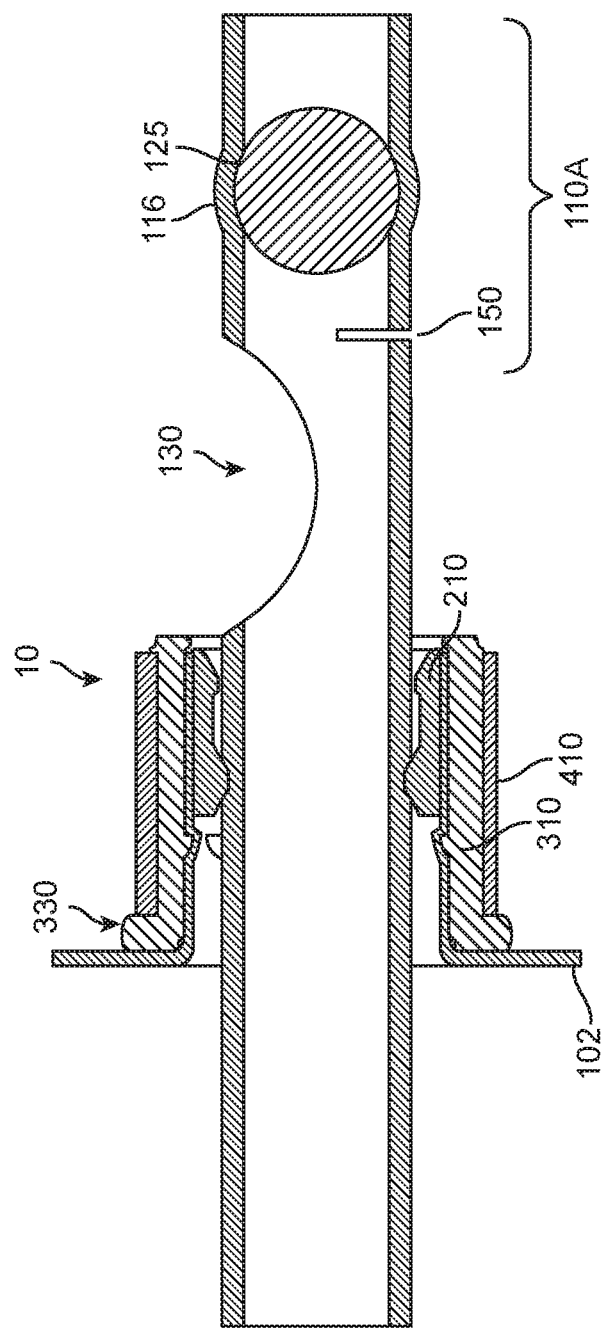

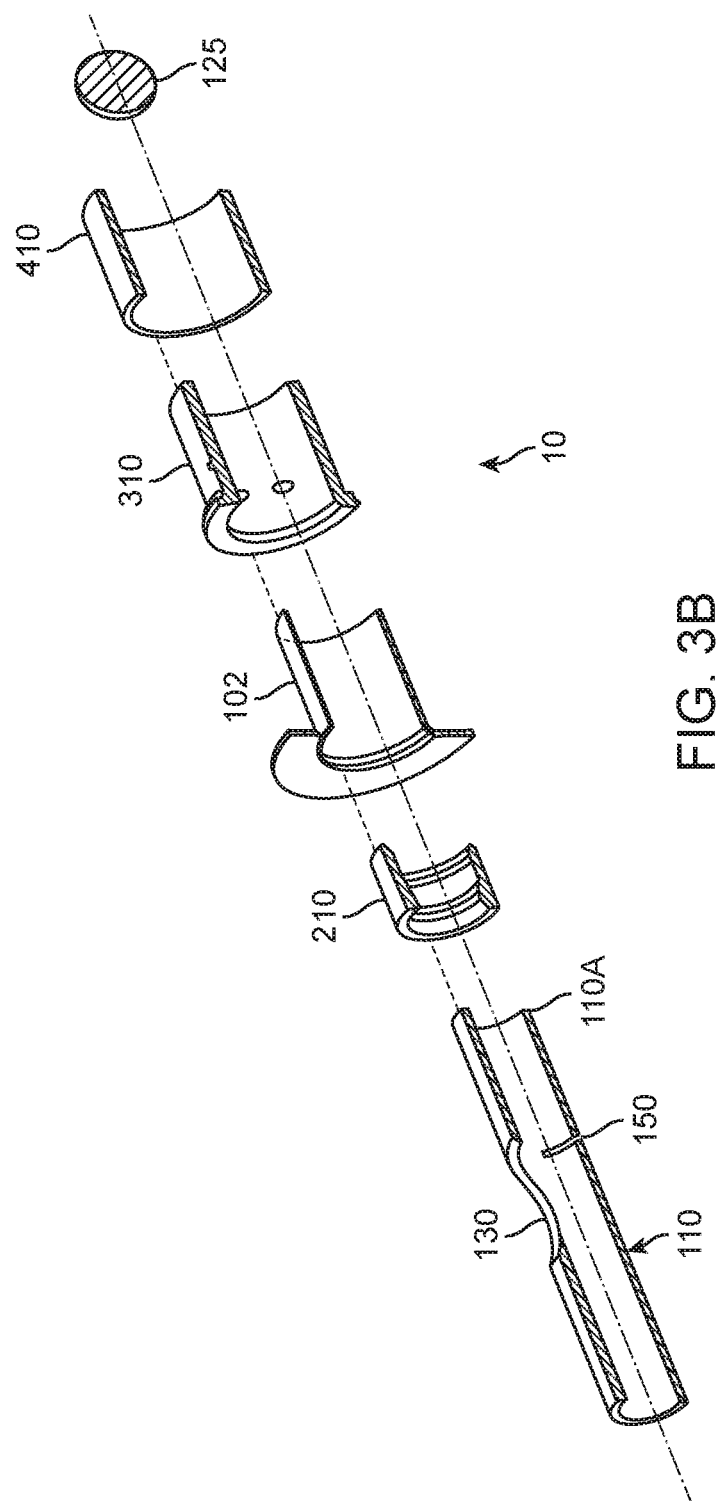

AUTOMATIC-SEALING BALLOON-FILLING CATHETER SYSTEM

CROSS-REFERENCE TO RELATED APPLICATIONS

This application is a non-provisional of U.S. Provisional No. 62/635,272 filed Feb. 26, 2018, the entirety of which is incorporated by reference. This application is also related to PCT Application PCT/US2019/019630, filed on Feb. 26, 2019, the entirety of which is incorporated by reference.

BACKGROUND OF THE INVENTION

The present invention generally relates to the field of balloon devices that occupy spaces within remote cavities and more particularly relates to the catheters/conduits used to inflate these devices with fluid.

One example of balloon devices that occupy space in a remote cavity is a intragastric balloon for weight loss. According to 2010 World Health Organization data, 198 million Americans over the age of 15 are above target weight. Of these individuals, 89 million are considered overweight (25<Body Mass Index<30) and 109 million are considered obese (Body Mass Index>30). Worldwide, more than 1.4 billion adults age 20 and over are overweight, and 500 million are obese. Obesity places patients at increased risk of numerous, potentially disabling conditions including type 2 diabetes, heart disease, stroke, gallbladder disease, and musculoskeletal disorders. Compared with healthy weight adults, obese adults are more than three times as likely to have been diagnosed with diabetes or high blood pressure. In the United States it is estimated that one in five cancer-related deaths may be attributable to obesity in female non-smokers and one in seven among male non-smokers (>=50 years of age). On average, men and women who were obese at age 40 live 5.8 and 7.1 fewer years, respectively, than their healthy weight peers.

For the vast majority of the overweight and obese population for whom surgical obesity procedures are not appropriate, few efficacious and affordable interventions are currently available. Diet and exercise remain the front line approaches to obesity, however this approach has at best slowed the growth of the epidemic. To date, drug therapies have dose limiting side effects or have lacked meaningful long term efficacy.

One less-invasive intervention that has begun to gain popularity is an intragastric balloon. Intragastric balloons in their uninflated state can be placed endoscopically or positioned using other methods and, once in place, are typically filled with a filling fluid through a thin catheter or conduit extending up the esophagus from the device in the stomach to an external fluid supply. This catheter is then removed from the device and extracted from the body through the esophagus. Upon removal of the catheter, the catheter fill system must seal the fluid communication between the interior of the device and the gastric environment to maintain the balloon in its filled state for the proscribed time.

Several approaches to sealing the catheter system have been developed. For example, in US20130012980 Brister describes the use of a septum, or rubber-like plug, through which a filling needle is disposed. Upon removal of the needle the rubber-like material elastically closes the puncture. While such a system is well-accepted for inflating athletic equipment such as footballs, it does require the hard, rubber-like septum to remain in the intragastric balloon for the life of the balloon.

Another approach for use in breast implants has been disclosed by Becker in US2010/0110311 in which a filling tube comprising a soft, flexible hollow tube portion and a barbed, solid distal portion is pre-installed through a piece of "semi-rigid tube" that penetrates the balloon wall. The filling tube has an outer dimension that is slightly larger than the inner dimension of the semirigid tube and is stretchable longitudinally to reduce the outer diameter to facilitate passage through the passageway in the semirigid tube. Supposedly, the outer diameter of the solid portion of the filling tube can be reduced by said longitudinal stretching to allow the solid portion to be pulled into the semi-rigid tube. The solid portion then sealingly engages the semirigid tube upon relaxation thereof. The significant force that must be applied to the filling tube to pull the solid portion into the semirigid tube apparently requires that the semirigid tube is attached to the balloon wall by a reinforcing disk of material. However, this construction prevents the balloon described by Becker from being compacted into an ingestible capsule when uninflated. The inventor further notes that expansion of the solid portion upon relaxation is not adequate to ensure the solid portion remains in the semirigid portion and that "A key element in the . . . invention resides in means such as a plurality of reverse barbs for preventing a plug valve from being dislodged . . . ."

Commonly assigned publication US20130218190, discloses a self-sealing tunnel valve comprising two layers of thin film material through which a flexible fill catheter is disposed. The two layers tend to close together upon catheter withdrawal. This tunnel valve is extremely soft and flexible, making it suitable for compaction into an ingestible capsule and for long term residence in the stomach.

It would be desirable to have a self-sealing valve that is small and/or soft enough to be compacted into an ingestible capsule while also providing a distinct sealed condition.

SUMMARY OF THE INVENTION

The present invention relates to devices and valve assemblies for remotely sealing an inflatable structure. For example, such devices can be used to occupying a space within a patient's body. In particular, the invention relates to catheter or conduit systems and methods for filling the devices and removing the catheter from the device and the patient's body without leakage of the filling fluid. In greater particularity, the present invention relates to catheter systems that automatically form a permanent seal for use in these space occupying devices.

In one variation, the present devices include valve assemblies. Such valve assemblies can be used with a balloon device (or any expandable device) having a fluid port. In one example the valve assembly includes a jacket member having an elongated shape, an outer surface and an interior channel, the interior channel comprising an engagement member; a wall anchor positioned within the balloon device and adjacent to the fluid port, the wall anchor having an interior passage that receives the jacket member, where a portion of the balloon device adjacent to the fluid port extends into the interior passage of the wall anchor and is secured between the outer surface of the jacket member and the interior channel of the wall anchor; a conduit (or catheter/tube) extending through the interior channel of the jacket member, the conduit having a fill end and a balloon end, wherein the conduit and the interior channel are configured to have a sliding resistance therebetween; the conduit having an interference region at the balloon end positioned within the balloon device, the interference region having a locking profile that allows the interference region to become fixedly engaged within the interior channel when moved therein; a weakened section located between the fill end of the conduit and the interference region, wherein the weakened section has a reduced tensile strength less than a tensile strength of the conduit while permitting sliding of the conduit relative to the interior channel upon the application of a pulling force on the conduit without causing separation at the weakened section, wherein the reduced tensile strength requires a tearing force to cause separation of the conduit at the weakened section; and a fill opening located on the conduit between the fill end and the interference region, the fill opening positioned within the balloon device such that fluid entering the fill end exits at the fill opening into the balloon, where the balloon end is occluded to prevent fluid from flowing therethrough, such that application of the pulling force that overcomes the sliding resistance causes movement the fill opening and the interference region into the jacket member to seal the balloon device.

Variation of the device can include a jacket member comprises an elongated cylindrical shape.

In another variation, the balloon end of the conduit includes a cylindrical plug having an external shaft diameter equal to or greater than an interior diameter of the conduit. The cylindrical plug can include a plug head sized to prevent movement through the interior channel of the conduit. In another variation, the cylindrical plug comprises at least one tooth comprising a tapered shape that increases a force required to remove the plug from the conduit.

A variation of the device can include a conduit that includes a spherical plug in the balloon end of the conduit, where an external diameter of the spherical plug is equal to or greater than an interior diameter of the conduit. The inter interference region can be adjacent to the balloon end.

Variations of the conduit can include one or more weakened sections located between the fill end and the interference region.

In another variation of the device, the interior channel of the jacket member includes at least one engaging element that reduces an interior diameter of the interior channel, wherein the interference region locks with the at least one engaging element to seal the interior channel of the jacket member.

Variations of the wall anchor can comprises a flared end adjacent to the balloon device.

The fill openings in the conduit can comprise a plurality of fill openings.

In additional variations, the portion of the balloon device can extending into the interior passage of the wall anchor extends to at least a length of the jacket member.

In variations of the device, a proximal face of the wall anchor is adjacent to but unconnected with a wall of the balloon device.

In yet another variation, a friction fit between the conduit and the interior passage of the jacket member creates a resistance between the conduit and interior passage of the jacket member that permits movement of the balloon device upon pulling the conduit.

The present invention also includes balloon device comprising one or more variations of the valve structure described herein.

The present disclosure also includes methods for sealing and releasing a fluid-filled balloon tethered to a conduit within a remote cavity and accessible through a passage. For example, the method can include retaining an end of the conduit outside of the passage, where the conduit is coupled to the fluid-filled balloon through a closure assembly, and where the conduit comprises a weakened section; applying a first extractive force to the conduit to overcome a frictional resistance between the conduit and the closure assembly causing the conduit to slide within the closure assembly until an interference region of the conduit engages the closure assembly, wherein the first extractive force is insufficient to separate the conduit at the weakened section; applying a second sealing force to overcome a sealing resistance between the interference region and the closure assembly to seat the interference region within the closure assembly to form a seal therebetween, where the second sealing force is greater than the frictional resistance but is insufficient to separate the conduit at the weakened section; applying a third detachment force, the detachment force being greater than the second sealing force, wherein application of the detachment force causes separation of the conduit at the weakened section; and withdrawing the conduit from the passage.

One variation of the method can further comprise applying a positioning force to the conduit, where the positioning force is less than the first extractive force and causes movement of the fluid-filled balloon and conduit within the remote cavity.

The methods described herein can include positioning the fluid-filled balloon against an anatomic structure in or surrounding the remote cavity, wherein the anatomic structure applies a physical resistance against movement of the fluid-filled balloon.

The resistance of the balloon member described herein can include a resistance against the balloon member when engaging a surface of the body cavity or a surface of the passage. Alternatively, or in combination, a fit between the conduit and the closure assembly can create a fluid seal at an interface of the conduit and the interior of the closure assembly. In another variation, a fit between the conduit and the closure assembly can creates a fluid seal at the closure assembly when the interference region is positioned within the interior of the closure assembly.

Yet another variation of a method described in the present disclosure includes a method for filling a space in a remote cavity within a body and accessible through a passage. Such a method can include retaining an end of a conduit outside of the body; advancing the conduit and a balloon member into the remote cavity through the passage, where the conduit is coupled to the balloon member through a closure assembly, and where the conduit comprises a weakened section positioned within the balloon member; delivering a fluid through the conduit into the balloon member to increase a size of the balloon member; initially applying a proximal force on the conduit such that a resistance of the balloon member causes the conduit to slide relative to an interior of the closure assembly until an interference region on the conduit contacts the interior of the closure assembly to provide a locking resistance, increasing the initial proximal force on the conduit to overcome the locking resistance and lockingly seats the interference region within interior of the closure assembly and seals the closure assembly and the balloon; further increasing the proximal force on the conduit cause failure of the conduit at the weakened section such that a section of the conduit proximal to the weakened section separates from the closure assembly and balloon member; and retracting the section of the conduit from the passage.

The present disclosure can also include catheter systems for use with fluid filled balloons for occupying a space within the patient's body. In one example such a medical device includes a liquid impermeable surface material forming a device body having an interior reservoir, the device body having a deployment profile and being expandable to an active profile upon receiving the liquid filler material within the interior reservoir; a fluid catheter comprising an extended section extending from the device to the exterior of the patient's body and a device section, the latter section passing through a fluid path, or catheter jacket, to provide a fluid filling material to the interior reservoir of the device body, where the catheter jacket is held in place in a wall of the device body by a balloon wall anchor, and where the extended section of the catheter is removable from the catheter jacket, such that upon removal of the extended portion of the catheter, the device section remains in the fluid path, which is thereby automatically closed to prevent liquid transfer to or from the patient's body.

The valves described herein provide a secure seal upon removal of the catheter from the device where the seal can optionally be permanent. The valves can include a design and materials that permit packaging in a compact configuration. Variations of the valves can be soft enough to be left in a patient's stomach for extended period without irritation to the stomach. Additional variations of the valve can reduce incidents of damage to the valve or associated device during manufacture or storage. Additional variations of the valve allow for balancing of material properties to allow for improved catheter removal by stretching and tearing at a designed tension.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

The foregoing and other objects, features and advantages of the methods, devices, and systems described herein will become apparent from the following description in conjunction with the accompanying drawings, in which reference characters refer to the same parts throughout the different views. The drawings are not necessarily to scale; emphasis has instead been placed upon illustrating the principles of the invention. Of the drawings:

FIG. 1A is a schematic block diagram of a fluid fillable balloon device.

FIG. 3A is a cutaway view of another variation of an ASCA.

FIG. 3B is an exploded cutaway view of the variation of an ASCA of FIG. 3A.

DETAILED DESCRIPTION OF THE INVENTION

The following illustrations are examples of the invention described herein. It is contemplated that combinations of aspects of specific embodiments or combinations of the specific embodiments themselves are within the scope of this disclosure. The methods, devices, and systems described herein can be used to improve gastric balloon devices. However, the devices, methods, and systems of the present disclosure can also be useful in other medical and non-medical applications that require a fluid-filled device with a removable filling system.

Figure 1B:
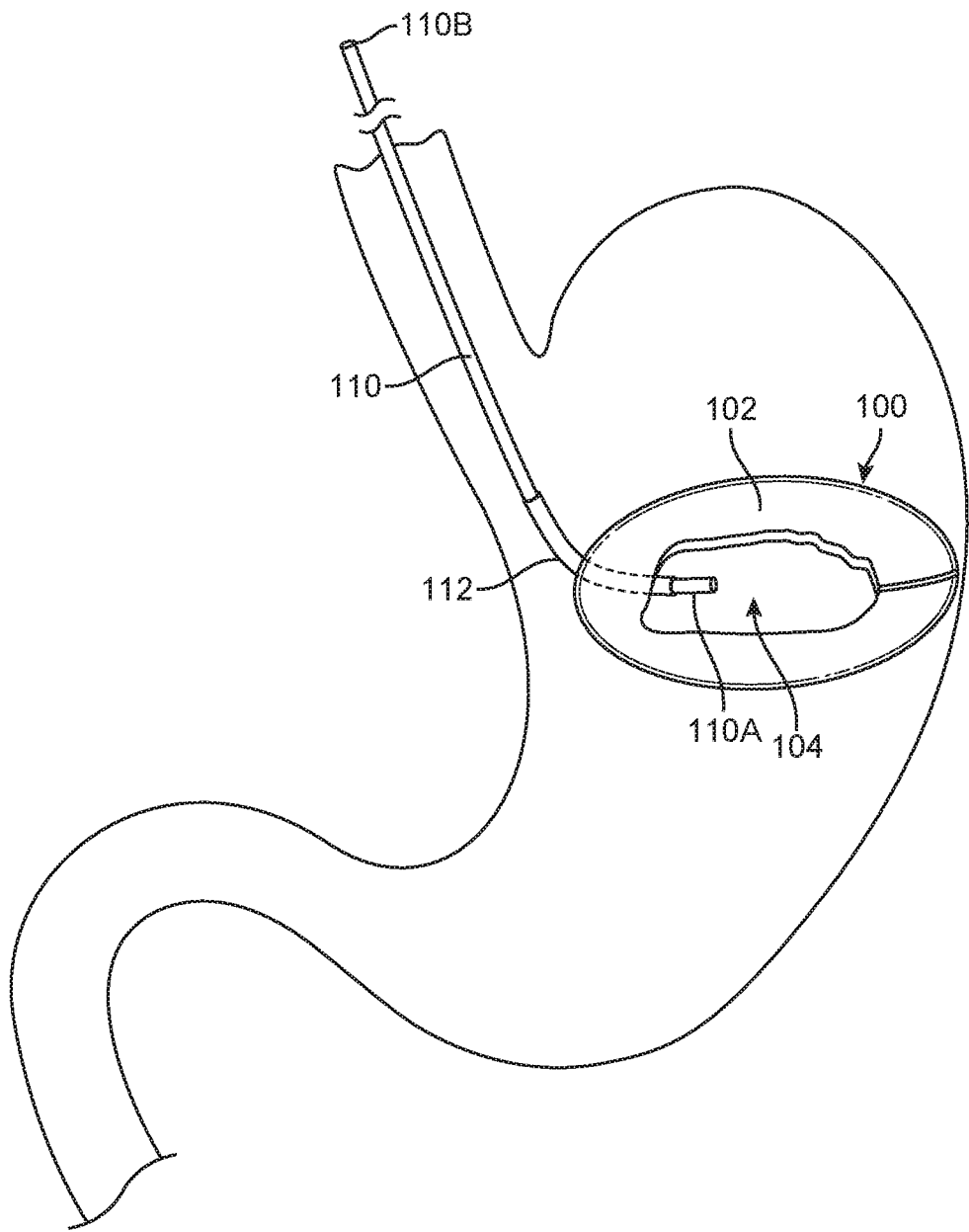
FIG. 1B illustrates a fluid fillable balloon device being filled.

FIG. 1A illustrates schematic block diagram of a fluid fillable balloon device 100; in particular, it illustrates a gastric balloon device assembly 100. FIG. 1B is an illustration of device 100 in place in a patient's stomach. The device generally comprises two states of interest: a pre-deployment or uninflated configuration and a deployed, inflated or active configuration; the deployed configuration is shown. Generally, the device is inflated with a fluid. For example, the fluid can be delivered through a tube 110 also referred to herein as a catheter or conduit, wherein the tube may pass through a lumen in the wall of the balloon device or is coupled to a fluid path 112 between the exterior and the interior of the balloon device. In alternative variations, the fluid can be delivered using any type of device that can deliver fluid. In many balloon devices a wall 102 of the balloon 100 is fabricated from a thin film material such as, for example, polyurethane. In some variations the tube 110 comprises a balloon end or internal section 110A that extends through fluid path 112 into the central enclosed space or reservoir 104 of device 100. In other variations internal section 110A stops before entering the reservoir or is just adjacent to the reservoir 104. The conduit 110 is removed from the device once inflation is completed. When the conduit is removed, fluid path 112 must be sealed to prevent the fluid from leaking out through fluid path 112 from reservoir 104. As shown schematically in FIG. 1A, sealing is accomplished by fill valve, which may comprise an internal section 113B, an external section 113A, or a combination of both. In some variations, elements of the fill valve 113 may have components installed inside conduit 110 as well as in fluid path 112.

Some variations of a gastric balloon device assembly 100 further comprise a fluid release valve 126. In some variations release valve 126 is independent from fill valve 113. However, in some variations, release valve 126 may be combined, at least in part, with fill valve 113. In some variations, release valve 126 reverses the operation of the sealing mechanism of fill valve 113.

Figure 2A:
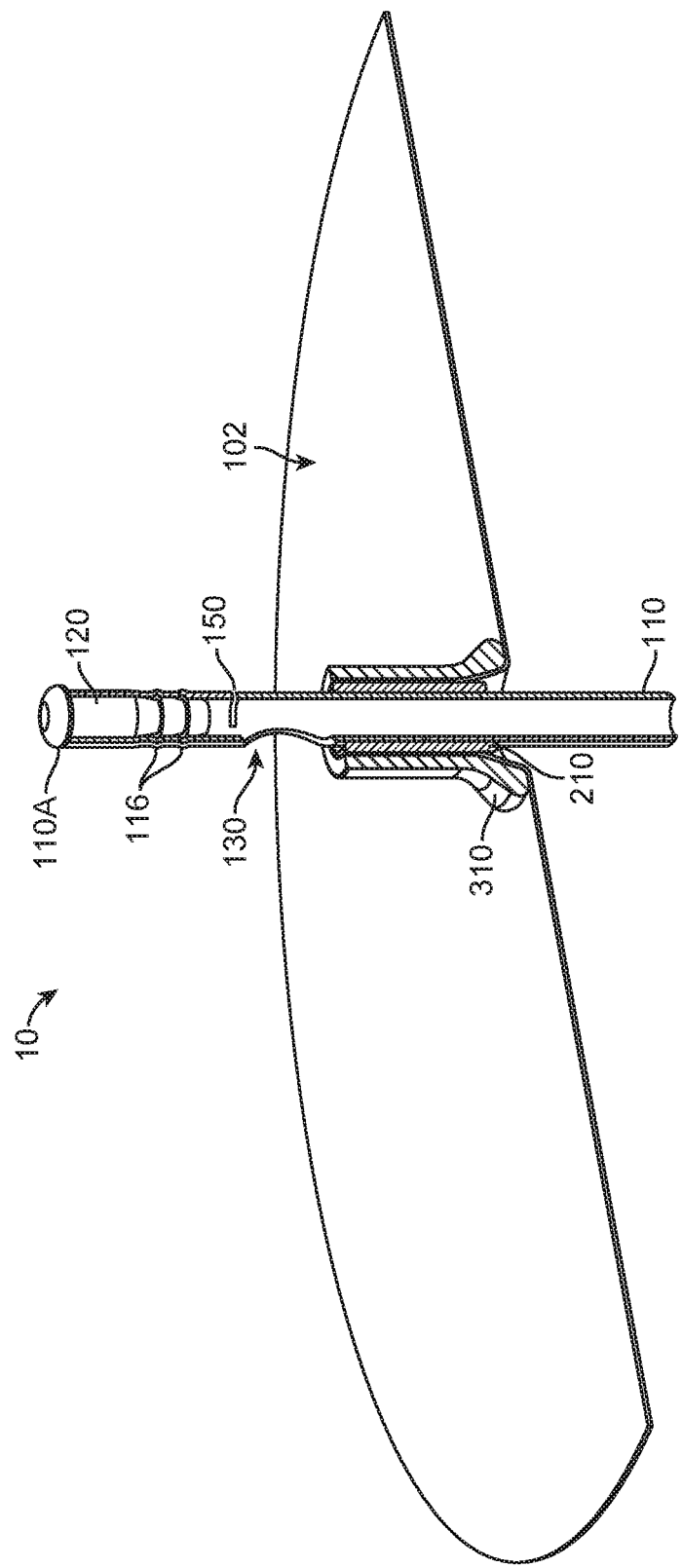
FIG. 2A is a cutaway view of a variation of an Automatic-Sealing Catheter Assembly ("ASCA") installed in a thin film wall of a balloon device.

In some variations, the fluid path itself serves as the fill valve, wherein the fluid path itself closes down to prevent fluid from escaping from reservoir 104. In other variations the fluid path is sealed by an automatic-sealing catheter assembly 10, which is a separate valve mechanism installed in the fluid path or in a portion of the conduit left behind in the fluid path when the main length of the conduit is withdrawn from the patient's body. FIG. 2A illustrates a partial cut-away view of one variation of the device 100 in the region of fill valve as it might appear within a patient's stomach, ready to be inflated. In this variation, the fill valve is an automatic-sealing catheter assembly (ASCA) 10. The variation shown in FIG. 2A includes a catheter 110 that extends from interior section 110A to outside of device 100, typically extending far enough to reach the exterior of the patient, where the balloon thin film wall 102 defines the division between the interior and the exterior of the device.

Figure 2B:
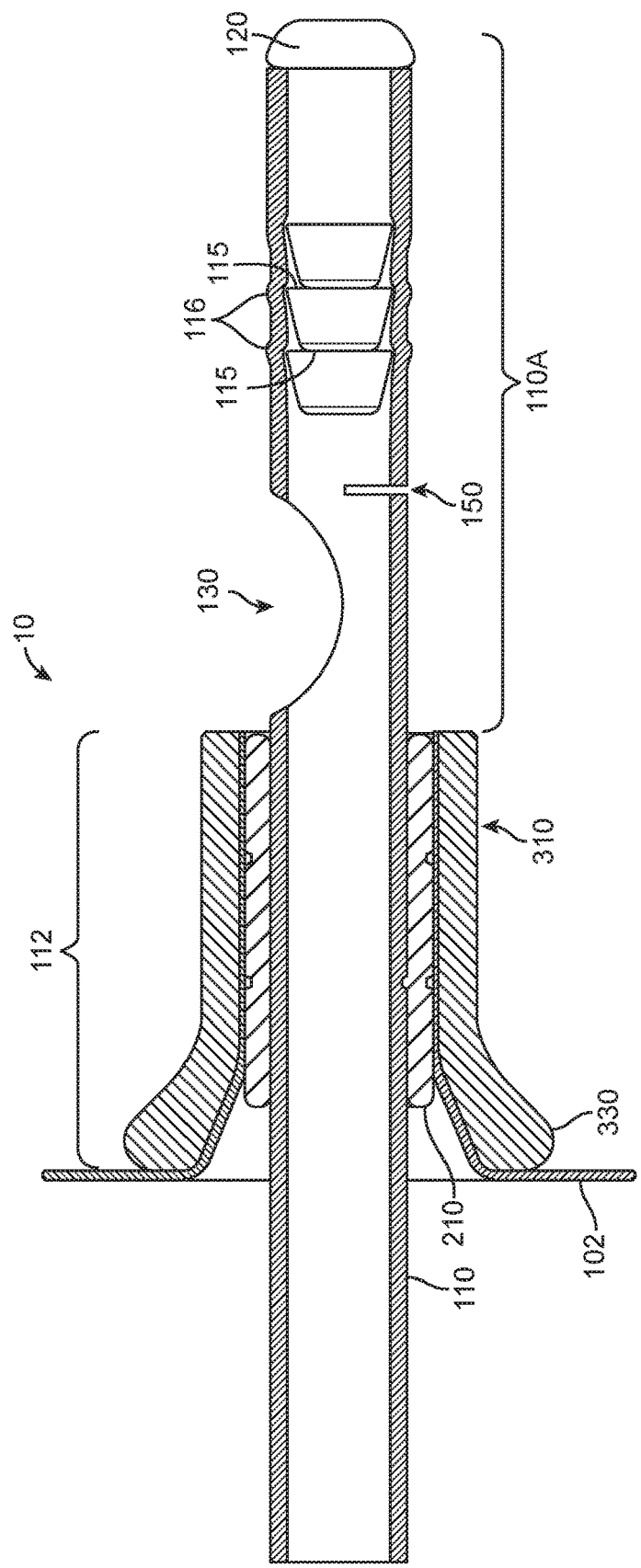
FIG. 2B is close up of the ASCA of FIG. 2A

FIG. 2B is a close up cutaway view of the ASCA 10 of FIG. 2A. The assembly comprises the internal section 110A of catheter 110, the end of which has been sealed shut with a plug 120, in this variation by a toothed plug 120, during assembly. The plug has one or more circumferential, or partially circumferential, teeth or projections 115 which create rings or bulges 116 that cause an increased diameter on the exterior of internal section 110A. The circumferential projections 115 also work to lock plug 120 into section 110A substantially permanently, although glue, welding, or other bonding approaches could be used to lock a plug into section 110A. The catheter further comprises one or more side-wall openings or fill ports 130, where the variation with one fill port is show in the figures, wherein the fill ports are disposed to be clear from plug 120 to allow filling fluid coming through the catheter to freely enter the balloon. In the illustrated variation, a catheter jacket 210 has been inserted through a section of balloon wall 102 from the exterior of the balloon and is held in place by pinching balloon wall 102 between the exterior of catheter jacket 210 and the interior of a balloon wall anchor 310. In the illustrated variation, the catheter further comprises a weakened section 150 designed to define where and with what tension the catheter will tear apart. In one variation, section 150 is a slit extending part way across conduit 110.

The cross-sectional view in FIG. 3A illustrates another variation of ASCA 10. In this variation, the toothed plug has been replaced with a spherical plug 125, for example a ball bearing. Also, in this variation a retaining ring 410 has been added to reinforce wall anchor 310. An exploded, cross-sectional view of the ASCA 10 of FIG. 3A is illustrated in FIG. 3B for clarity.

Figure 4A:
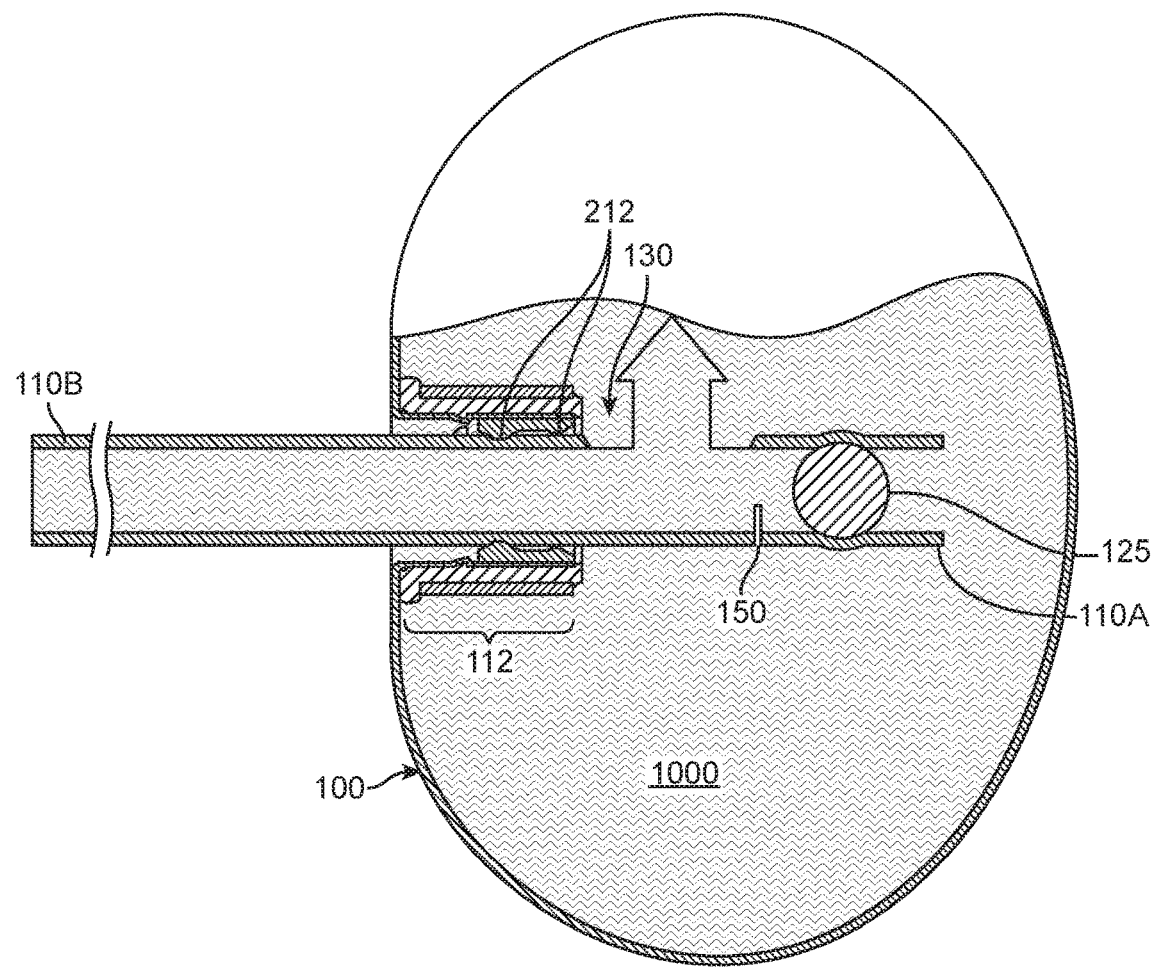
FIG. 4A illustrates a variation of the ASCA while a balloon is being filled.

FIG. 4A illustrates an example of the automatic-sealing behavior of the catheter assembly of FIG. 3. FIG. 4A illustrates ASCA 10 as fluid enters a balloon device 100. As has been discussed above, balloon 100 is inflated by injecting a fluid 1000 at a catheter fill end 110B. The fluid travels the length of the catheter and exits the catheter through a catheter fill port 130 disposed proximate or, in close proximity to, a catheter balloon end 110A, where the catheter balloon end 110A is intended to be inserted far enough into the balloon such that the fill port 130 is completely unobstructed by the other components of the variation of ASCA 10. Of course, if this condition is not met the balloon will still inflate if at least a portion of the port is unobstructed, albeit at a slower rate. After a proscribed volume of fluid has been injected into the balloon, or, alternatively, a proscribed back pressure of the fluid has been reached, catheter 110 is withdrawn from the patient. However, to maintain inflation of the balloon 100 fluid path 112, which normally would allow two-way fluid flow, must prevent exit of the fluid to prevent deflation of the balloon.

Figure 4B:
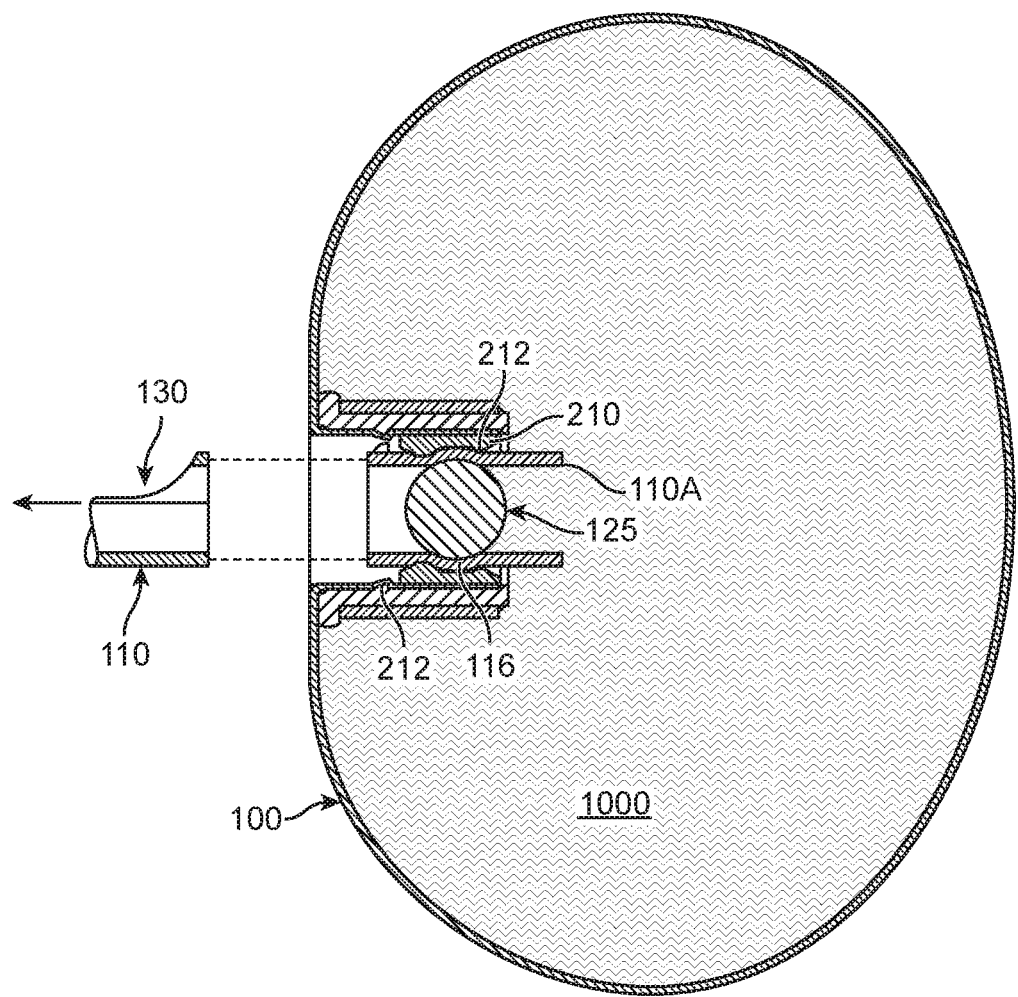
FIG. 4B illustrates the ASCA of FIG. 4A in its sealed configuration after a balloon is filled.

FIG. 4B illustrates a partially withdrawn catheter 110 in a sealing position. As shown, catheter 110 has been pulled into catheter jacket 210 until it moves plug 125 between the engagement elements 212 built into the inner surface of jacket 210. In the illustrated variation, catheter 110 is secured in the sealing position when catheter wall bulges 116 formed by plug 125 abut engagement elements 212, which, in this variation, are ridges in the inside of catheter jacket 210. In this configuration the fill port 130 is no longer in fluid communication with the interior of the balloon and the exterior of the catheter is compressed between the internal ridges and the plug, in this case operating like an o-ring, effectively sealing the catheter assembly. Once the catheter balloon end 110A has been secured in the catheter jacket, any further increase in axial tension on the catheter are applied to tear the catheter to allow the majority of catheter 110 to be extracted from the patient while leaving catheter balloon end 110A in catheter jacket 210, as indicated in FIG. 4B. By design, tear-away slit 150 (shown in FIG. 3B) creates a unique location at which the catheter will tear; additionally, by design, the force at which the catheter tears can be adjusted to any reasonable value by varying the depth or shape of slit 150.

Figure 5A:
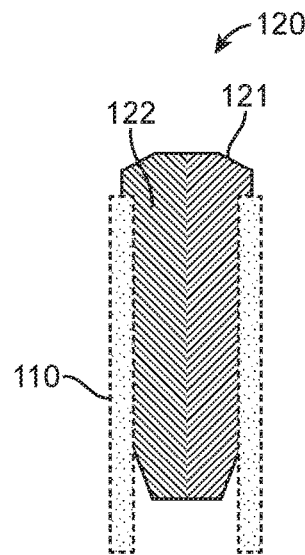
FIGS. 5A-5G illustrate seven variations for a plug for an ASCA.
Figure 5B:
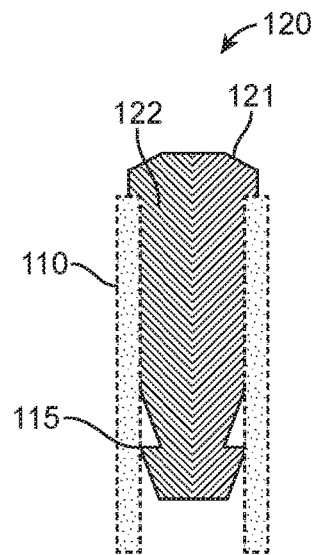
Figure 5C:
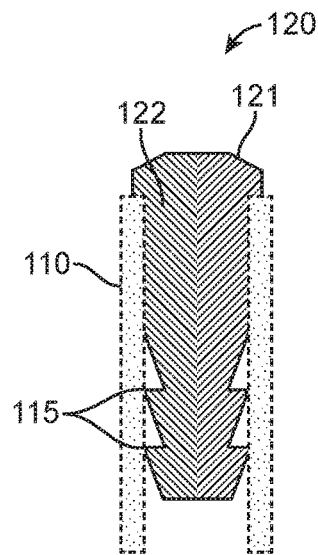
Figure 5D:
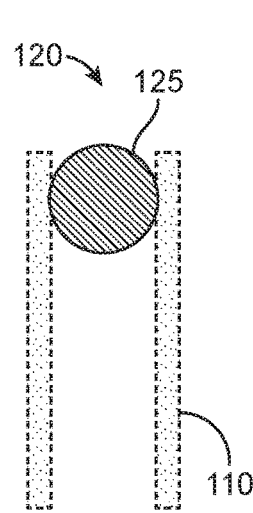
Figure 5E:
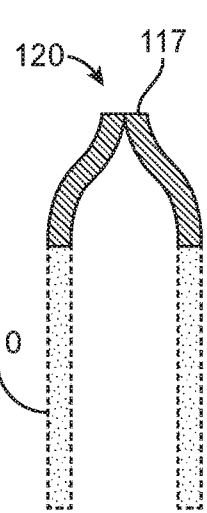
Figure 5F:
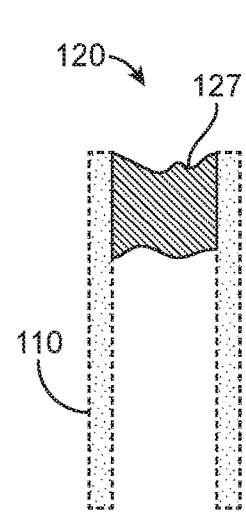
Figure 5G:
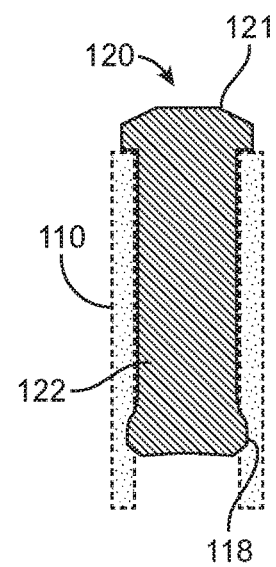

Each of the elements of the ASCA can take multiple forms that effect the same results. For example, as shown in FIG. 5A through 5g, plug 120 can have just one (FIG. 5B), instead of two (FIG. 5C), circumferential teeth 115, or a plug shaft 122 can be smooth sided (FIG. 5A). In other variations plug 120 can be a small ball bearing 125 (FIG. 5D) or the plug can be a measured amount of hardening material, for example, glue 127 injected into the end of the catheter 110 (FIG. 5F) or the distinct plug can be replaced by simply sealing the balloon end of catheter 110 (FIG. 5E). This seal can be effected by pinching the open end 117 of the catheter and thermally sealing it closed, by gluing it closed, or by any other convenient means for eliminating a distinct plug component. In yet another variation, shown in FIG. 5G, plug 120 includes a shaft 122 that is generally smooth sided except for a bulbous protrusion 118 at its tip.

In many variations plug 120 comprises plug shaft 122 and a plug head 121 wherein plug shaft 122 has a main diameter substantially equal to the interior diameter of catheter 110 while plug head 121 has a diameter larger than the internal diameter, $ID_C$, of catheter 110 to facilitate insertion and/or removal of plug 120 from the catheter and, in some variations, plug head 121 has a diameter larger than the external diameter of catheter 110 to improve retention of the catheter balloon end 110A inside balloon jacket 210 as the major portion of the catheter is removed from the patient's body. In some variations the plug shaft 122 comprises one or more teeth 115 wherein the teeth are disposed to permit plug 120 to be inserted into catheter balloon end 110A with relatively little extra resistance but are shaped to dig into the relatively soft catheter material when force is exerted in the direction to extract plug 120 from catheter 110. Furthermore, for reasons discussed below, the diameter of the teeth is, by design, selected to form localized expanded bands, rings, or bulges 116 around the exterior of catheter 110. The region having these expanded bands is the interference region, so-called because the region has a mechanical interference with the engagement elements in jacket 210.

Plug 120 may be fabricated from any substantially incompressible, bio-compatible material. In one variation the plug is fabricated from stainless steel. In one variation in which a ball bearing is used as plug 120 the diameter of the ball bearing is designed to provide substantially the same functions as a toothed plug, that is, the diameter of the ball bearing is slightly larger than $ID_C$, thus both plugging catheter 110 and forming one expanded band around the exterior of catheter 110.

Figure 6A:
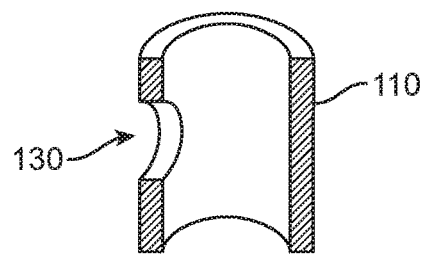
FIGS. 6A-6C illustrate three variations of fill ports for an ASCA.
Figure 6B:
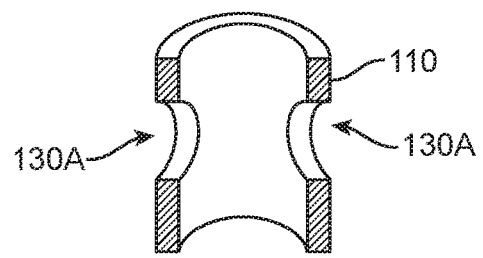
Figure 6C:
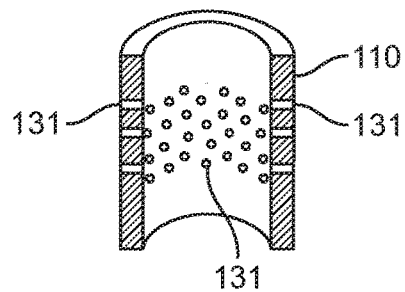

Similarly, as shown in FIG. 6A through 6C, fill port 130 illustrated in FIG. 2 can be functionally replaced by other designs. FIG. 6A illustrates a single fill port 130 in catheter 110, whose size is determined by the net port open area designed to fill the balloon without creating excessive back-pressure or slow fill rates. In FIG. 6B the single fill port replaced by two or more, possibly smaller, ports 130A. These two ports are shown as diametrically opposed but they may be located anywhere around catheter 110. Further, port 130 can even be replaced by micro-drilled perforations 131, as shown in FIG. 6C, in a band around the catheter 110, this latter approach maintains rotational symmetry of the structure of the catheter 110 while still providing the desired net open area in the catheter. Laser micro machining by a vendor such as Resonetics, 44 Simon St. Nashua, N.H. can be advantageously used to create these small, closely packed openings 131 in the catheter material.

FIG. 7 illustrates in cutaway variations of catheter jacket 210. In its most basic configuration, not illustrated, jacket 210 comprises a rigid cylindrical tube. In some variations jacket 210 has an internal diameter smaller than the catheter's outer diameter by a small amount, say 0.010 inches. In many variations, jacket 210 further comprises one or more raised engagement elements 212, wherein the elements 212 may be distinct bumps, knobs, or teeth, as shown in FIG. 7B, or they may be continuous ridges or rings as shown in FIG. 7A. In all cases engagement elements 212 reduce the internal clearance of the jacket to be less than catheter's 110 outer diameter to provide frictional engagement, or mechanical interference, between the jacket 210 and the interference region of catheter 110. In some cases, the engagement element can gently dig into the exterior of catheter 110. This diametrical difference is preferably between 0.001 inches and 0.050 inches; more preferably between 0.005 inches and 0.020 inches; and most preferably between 0.006 and 0.010 inches In some variations one or more of these raised elements may be asymmetric relative to the axis of symmetry of jacket 210, that is, the interior edge 214 and the exterior edge 216 may have different slope angles. In one variation the interior edge 214 is sloped to facilitate pulling catheter balloon end 110A from the exterior side into jacket 210 to seal the ASCA while exterior edge 216 is more perpendicular to the interior wall of jacket 210 to inhibit, but not preventing, catheter balloon end 110A from moving inwardly after the rest of catheter 110 has been torn away.

Figure 7A:
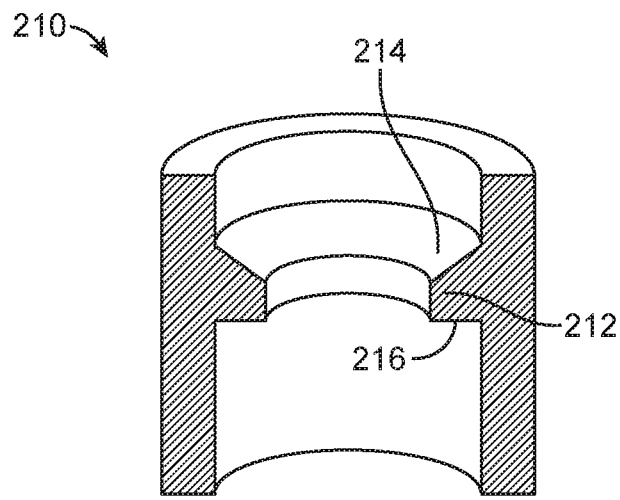
FIGS. 7A-7C illustrates three variations of a wall a for an ASCA.
Figure 7B:
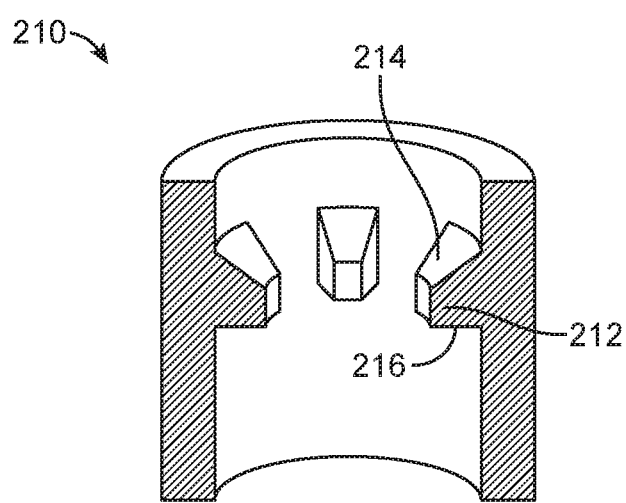
Figure 7C:
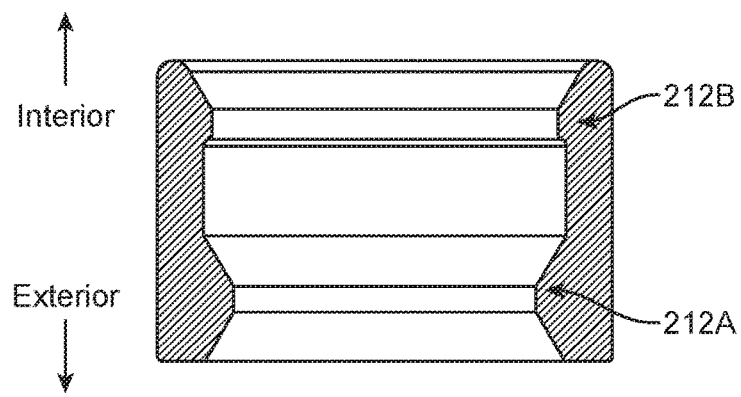

In other variations, as suggested in FIG. 4B, other engagement elements 212 may be configured to help form a fluid tight seal when plug 120 is pulled into jacket 210. In some variations, as shown in FIG. 7C, there may be two or more sets of engagement elements. The outermost (that is, closest to the exterior of balloon 100) engagement elements 212A have a small enough inner diameter to prevent plug 120 (shown as ball bearing 125 in FIG. 4B) from being pulled out jacket 210 when catheter 110 is extracted, whilst innermost elements 212B prevent plug 120 from migrating back into balloon reservoir 104 once the plug is in the sealing position. Innermost elements 212B also help to form a fluid-tight seal by squeezing plug 125 against outermost elements 212A when there is a compressible section of catheter therebetween.

That is, some of engagement elements 212 are configured to compress and dig into catheter 110 to hold catheter balloon end 110A inside gastric device 100 under small, incidental extractive loads but not retain catheter balloon end 110A inside the gastric device under the larger, intentional extraction load used to detach the catheter from the device. As illustrated in the graph in FIG. 7D, the frictional force holding a prototypical polymeric catheter back from extraction generated by outermost or exterior engagement elements 212A of a compatibly designed jacket may be determined at the time of design to span a wide range.

Figure 8A:
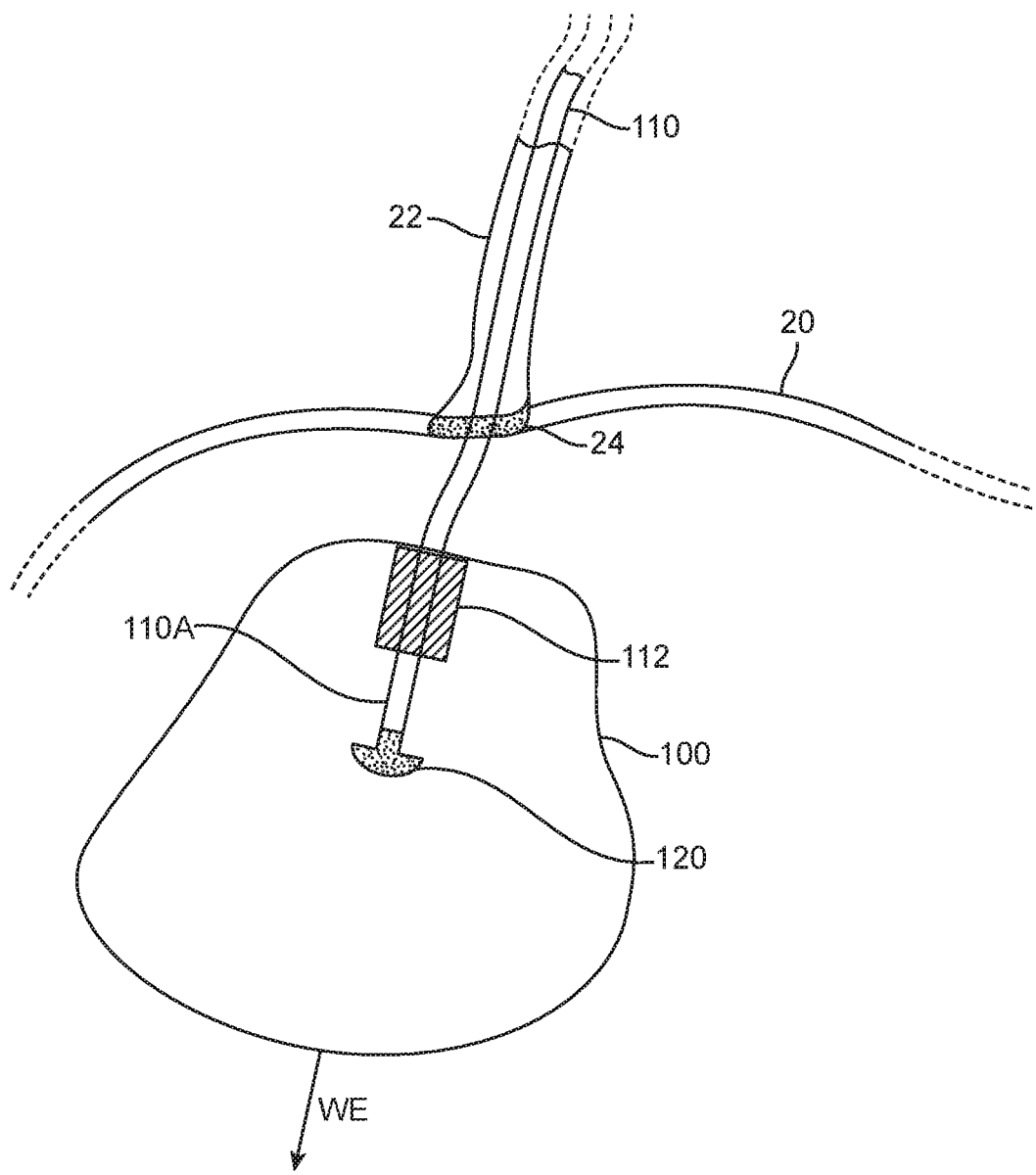
FIGS. 8A to 8C illustrates an example of a deployment process of a device and valve assembly.
Figure 8B:
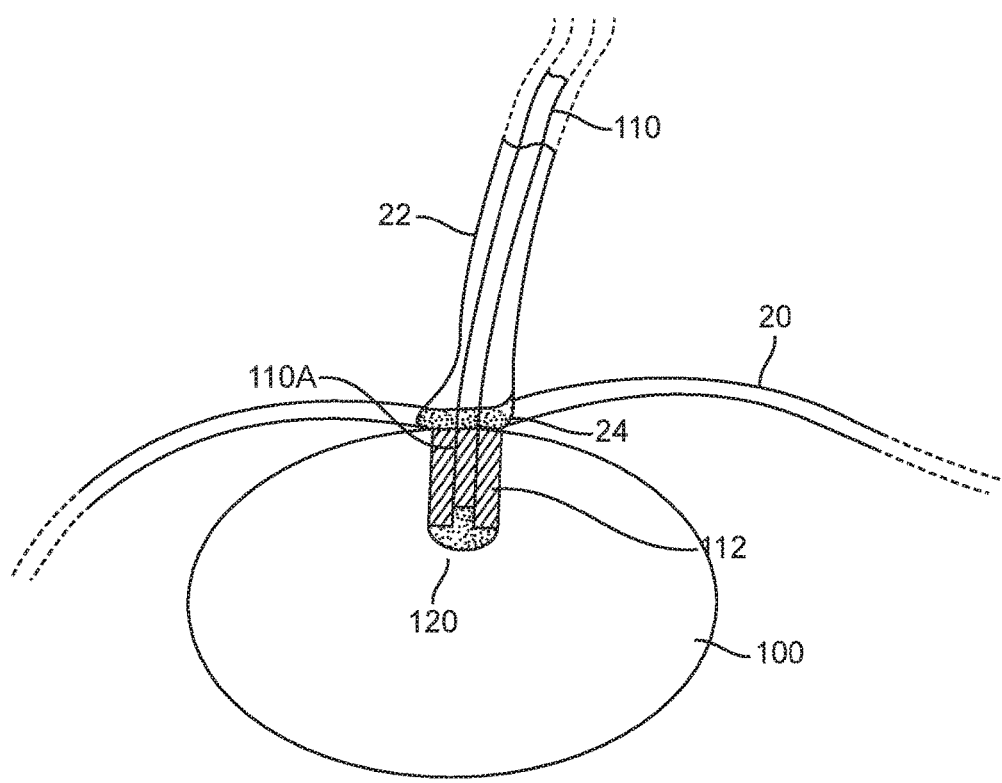
Figure 8C:
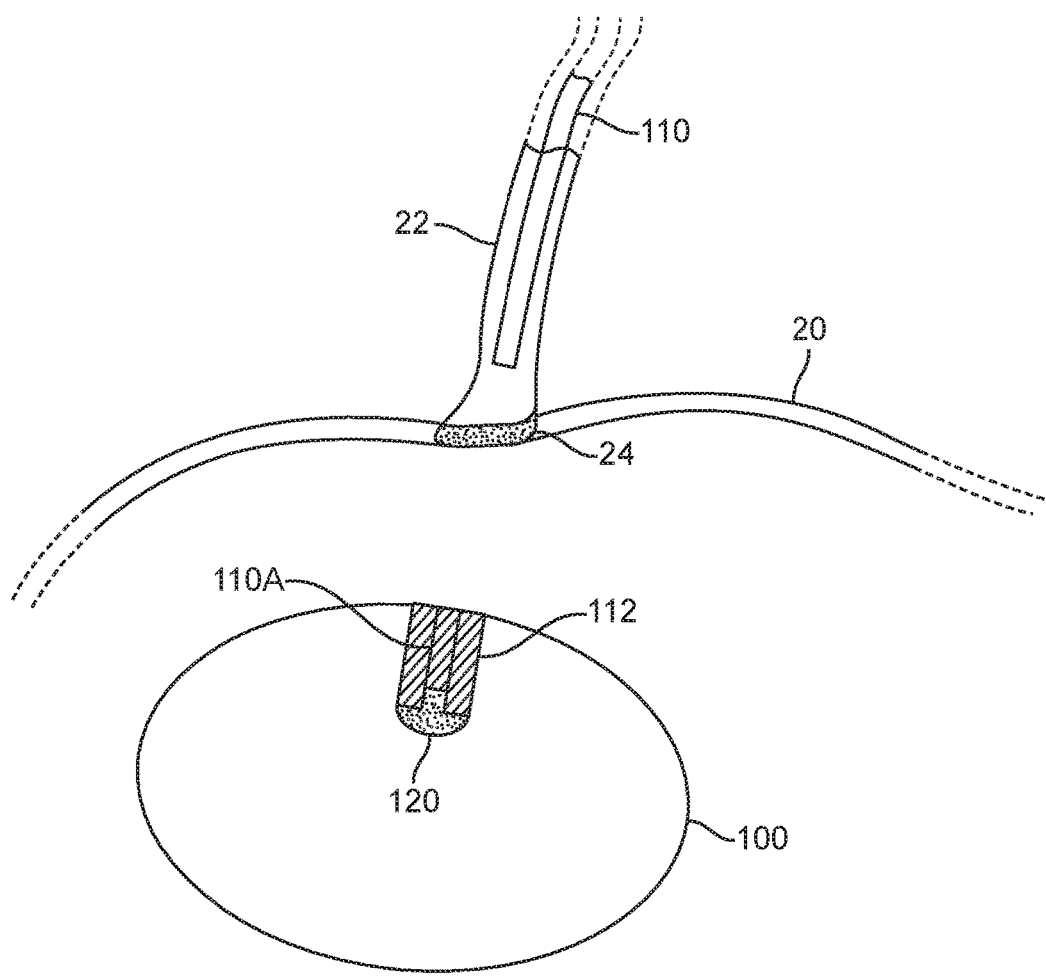

In general, the elements that comprise the ASCA are intended to control the frictional/retention force that holds the catheter 110 in the ASCA during the deployment process. As illustrated in FIGS. 8A-8C, for purposes of illustration, there are three stages in the deployment process, where the maximum retaining force that holds the catheter within the device varies in each stage. As shown in FIG. 8A, for a gastric balloon variation, the first stage that occurs after positioning the device in the stomach 20 is a filling stage, during which the medical caregiver begins to infuse fluid into the empty device 100 (or partially empty device). During this stage, device 100 can be considered as a weighted mass at the end of the catheter 110. As device 100 fills with fluid, especially when the fluid is a liquid, the weight of the balloon 100 increases from the weight of just the un-inflated thin film balloon. In one variation, the filled balloon weight ("WB") is approximately 500 grams. In some variations, the filled device is at least partly supported by surrounding tissue or, in the case of a gastric balloon, by the contents of the stomach, which reduces the effective weight applied by the balloon on the catheter. To keep device 100 from pulling away from, or sliding off, catheter 110 before the filling process is completed, the force that retains the catheter within the valve (the sliding resistance threshold or retention force "FR") must be greater than the effective weight ("WE") or else the weight of the balloon could cause pre-mature detachment of the catheter or sealing of the valve.

As shown in FIG. 8B, a second stage of the deployment process seals the ASCA. Closing this valve requires pulling balloon end 110A of catheter 110 into fluid path 112 such that the fill port 130 is withdrawn from the reservoir of the balloon 100. As illustrated, this stage of the process comprises pulling the catheter 110 in a proximal direction (e.g., towards the esophagus 22) until filled device 100 encounters resistance to motion against the esophageal sphincter 24. Once device 100 abuts sphincter 24, continued application of the proximal force increases the tension in catheter 100 until the tension is greater than, and overcomes, the FR, allowing the catheter internal end 110A to slide into fluid path 112 with a sliding resistance somewhat below the sliding resistance threshold. This movement closes the valve. The force required to overcome FR is the called a "closing force" or "FC". In general, the FC is a "threshold" force, meaning that once FC overcomes FR, the force required to maintain movement of the catheter will be less than FC, since sliding friction is less than static friction/resistance.

As catheter 110 is pulled into fluid path 112, plug 120 reaches engagement elements 212A (not shown in FIG. 8A) and cannot move any further.

As illustrated in FIG. 8C, the majority of catheter 110 is disconnected from device 100 and removed from the patient's body. Only internal section 110A, which is part of ASCA 10, remains in device 100 after device deployment. With the device lodged against esophageal sphincter 24 the disconnection of catheter 110 is effected by pulling on the catheter with increasing force until the tension in catheter 110 exceeds a tear force, FT, which causes the catheter to separate at weakened section 150, in this variation a slit, where the depth of slit 150 has been designed to keep the tear force FT below a force, FE, that would damage the esophageal sphincter. Note that in some variations tear slit 150 is replaced by other means of weakening the catheter at the desired tear location to achieve a safe disconnection of catheter 110.

Figure 7D:
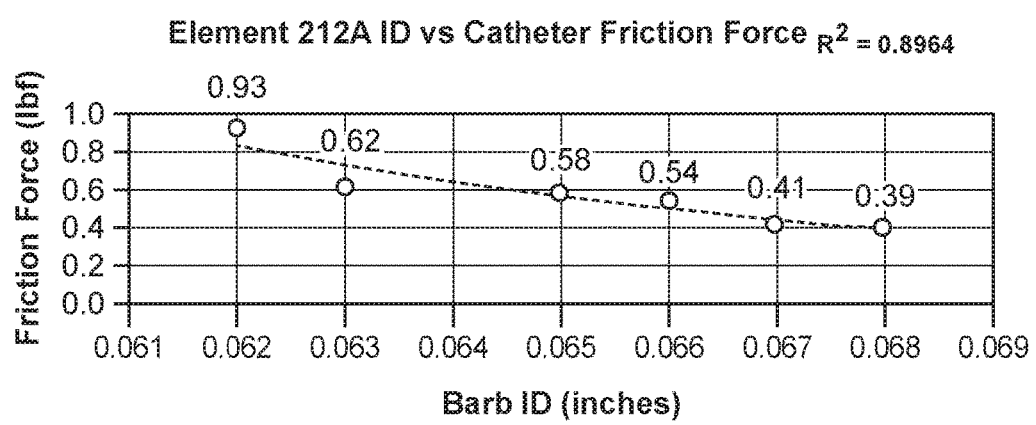
FIG. 7D illustrates the relationship between the interior diameter of the exterior engagement element of FIG. 7C and the frictional force holding a catheter in place.

The primary means of controlling the various forces are the material properties of the catheter material and the internal diameters and profiles of the internal features of catheter jacket 210. For example, FIG. 7D illustrates the relationship between the internal diameter of an engagement element ("Barb ID") and the frictional force/resistance felt by a catheter, as measured for an exemplary embodiment of element 212A and catheter 110.

During the design of ASCA 10, several relationships must be considered. First, to prevent the catheter from moving during the balloon fill stage of deployment,

FR>WE.

Second, to initiate the closing of the ASCA by starting the catheter moving into the catheter jacket,

FC>FR.

Third, to prevent injury to the patient,

FT<FE, and

FR<FE.

Finally, to prevent the catheter from tearing before the valve is closed

FT>FC.

Based on experimental experience which determined both the WE and the FE, in one variation FR is preferably, 0.25 lbf<FR<1.6 lbf and more preferably 0.6 lbf<FR<1.1 lbf. where 1.6 lbf was determined to be safely below FE for human patients. Further, 1.25 lbf<FT<1.6 lbf. Note that FC is not a free design parameter because it is always equal to the FR of the specific as-built valve. (that is, the valve starts closing as soon as FC exceeds the threshold of FR).

The construction of the device shown above, with the various range of forces is especially useful in those situations such as a gastric device where deployment, filling, sealing, and detachment occurs remotely within the stomach. In such a case, it is desirable to close the valve and detach the conduit without supporting or holding the valve by supplementary means. Since the device is within the stomach, providing support to the valve or cutting the catheter would require a tool advanced through the esophagus causing the procedure to increase in complexity.

Figure 7E:
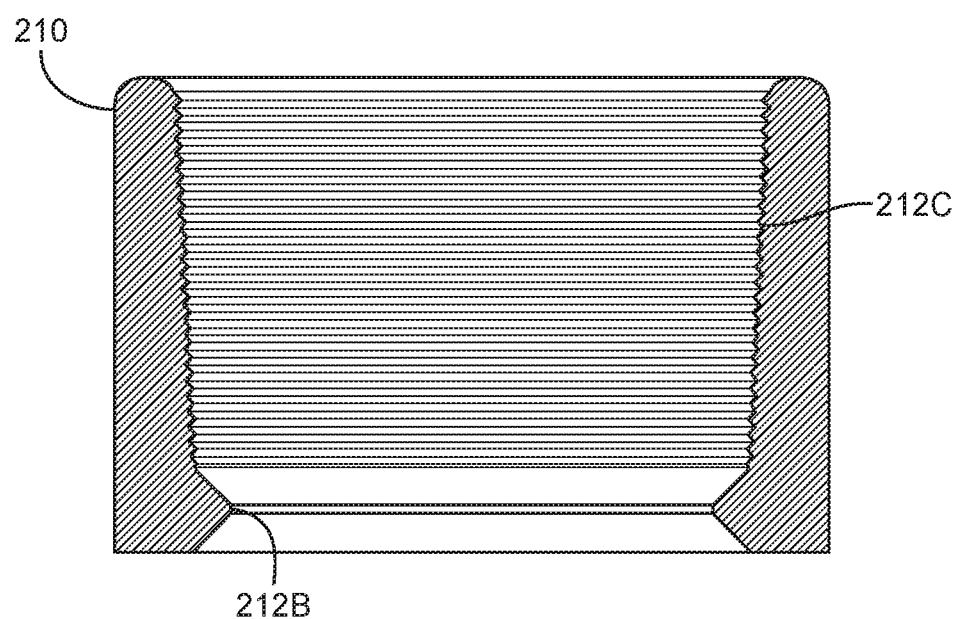
FIG. 7E is a cutaway view of another variation of a catheter jacket.

Another variation of a catheter jacket is illustrated in cutaway view in FIG. 7E. In this variation the distinct engagement elements of previous variations are replaced by closely spaced, tapered internal diameter ridges 212C. These ridges apply an increasingly tight grip on the catheter as catheter balloon end 110A is pulled further outwardly, whereas engagement elements 212A tend to grip the catheter with a constant force, independent of how far the catheter has been pulled.

In some variations, as illustrated previously, jacket 210 is affixed to a portion of the balloon wall material, either a free-standing patch or a relatively smooth portion of the actual balloon wall at, for example, a polar region of an oblate spheroid balloon. In other variations, jacket 210 can be fabricated from a short piece of polymer tubing such as polyurethane, which is compatible with welding or gluing into an equatorial seam between two halves of a polymer, for example polyurethane, balloon.

Figure 9:
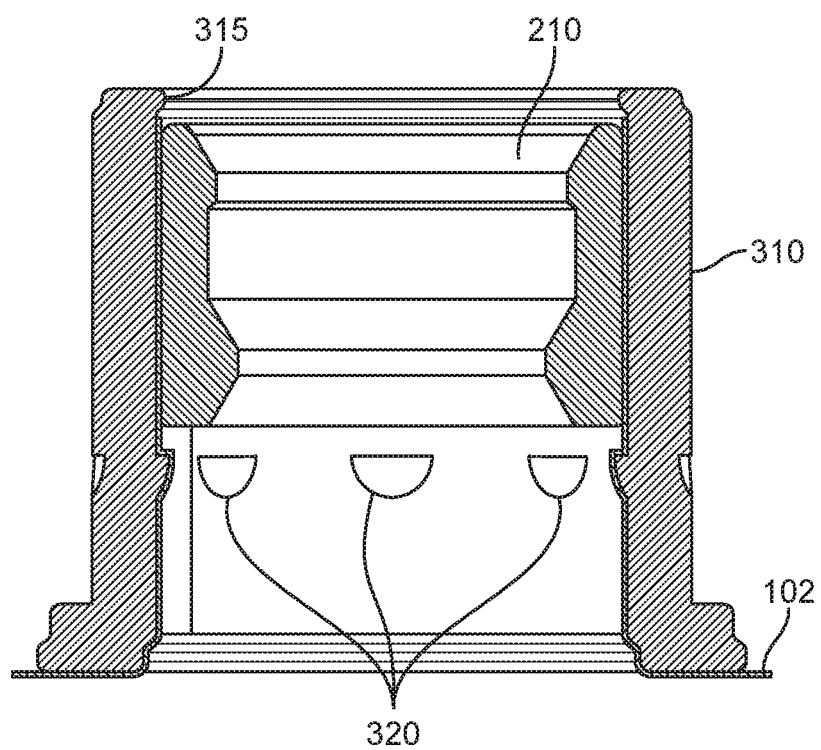
FIG. 9 is a cutaway illustration of a balloon wall anchor for an ASCA.

In some variations jacket 210 may be held in place by a balloon wall anchor 310. In variations utilizing a balloon wall anchor, the thin film of material (either in the form of a section of the balloon wall 102 or a separate patch of material) is pinched between catheter jacket 210 and balloon wall anchor 310, locking catheter jacket 210 in place in the balloon wall. As shown in FIG. 9, anchor 310 may comprise one or more internal rings or teeth 320 to lock jacket 210 in place. In the variation shown in FIG. 9, anchor 310 comprises an inward-facing lip 315 which prevents catheter jacket 210 from entering the interior of the balloon device. Further, anchor 310 comprises inward facing nubs 320 that are shaped to allow jacket 210 to slide over them when being inserted from the exterior side of the balloon but which lock it in place once the end of the jacket passes the edge of the nubs. Additionally, some variations of anchor 310 comprise a flared exterior facing end 330, as shown in FIGS. 2B and 3A. Flaring this end of wall anchor 310 provides a smooth and expanded contact surface between the anchor and the thin-film wall material, reducing the probability of tearing the wall material. In some variations anchor 310 is fabricated from polymer material to reduce the probability of damage to the thin film wall material 102, which is sandwiched between jacket 210 and anchor 310.

As shown in FIG. 3B, in some variations of the ASCA a retaining ring 410 is installed over balloon wall anchor 310. In some variations retaining ring 410 comprises a thin walled, stiff cylindrical tube with a close inner diameter-to-wall anchor outer diameter tolerance designed to capture the thin film wall material in a press fit. In variations with a soft anchor, the retaining ring provides the creep resistance and stiffness normally found in a metal wall anchor. An advantage of this variation is that a metal catheter jacket, for example stainless steel, can be pressed through the region of thin-film wall material and up into the soft/compliant wall anchor without the force from the press fit causing the film to shear. The soft wall anchor acts as a cushion for the film between a stiff, metal catheter jacket and a stiff, metal retaining ring so that a strong press fit can be achieved.

The ASCA can be fabricated on a separate patch of balloon-compatible material or assembled in situ in a wall of the balloon device. A process for fabricating the automatic-sealing catheter assembly typically comprises the following steps:

1) Identifying a region of thin-film material balloon wall suitable for installation. Such region is typically substantially flat and approximately 45 millimeters in diameter. In some applications in which the balloon is a highly oblate spheroid this region may be at one of the poles of the spheroid. In other variations the installation region may be on a separate patch of material known to be compatible with the thin film material of the balloon. In typical variations the patch of material is between 0.0025 and 0.005 inches thick. The patch of material will later be installed over a hole in the balloon device in a region that is typically substantially flat, such as at one of the poles of a highly oblate spheroidal balloon. In certain variations the installation region may be on a seam in the balloon wall.

2) Placing the thin film material in a fixture comprising two rigid plates, each of which have a central through hole with a diameter commensurate with the catheter jacket. The material region is sandwiched between the two plates and typically centered on the through hole.

3) Pushing the jacket up through the hole from a first side of the fixture, stretching the film over the jacket in the process. The first side of the fixture corresponds to the exterior of the balloon and defines an exterior side of the finished ASCA.

4) Pressing the wall anchor over the jacket and film from a second side of the fixture, captivating the film between the jacket and the wall anchor. The second side of the fixture corresponds to the interior of the balloon.

5) Removing the jacket-film-anchor subassembly from the rigid plate assembly.

6) Optionally pressing the retaining ring over the subassembly from what had been the second side of the fixture. The retaining ring should be bottomed out against the end of the wall anchor.

7) Separately, preparing the catheter balloon end. Typically, this preparation comprises:
   a. Creating one or more fill ports.
   b. Cutting one or more tear-away slits.

8) Inserting the prepared catheter balloon end into the subassembly from the exterior side of the ASCA, allowing the balloon end to project past the end of the rest of the subassembly by a convenient working distance but at least far enough to expose the fill port(s).

9) Inserting the plug into the open lumen of the catheter balloon end or, alternatively, sealing the open lumen of the catheter balloon end.

10) Withdrawing the catheter from the exterior side of the ASCA to eliminate excess catheter length on the interior side of the ASCA, leaving the fill port(s) exposed.

Figure 10:
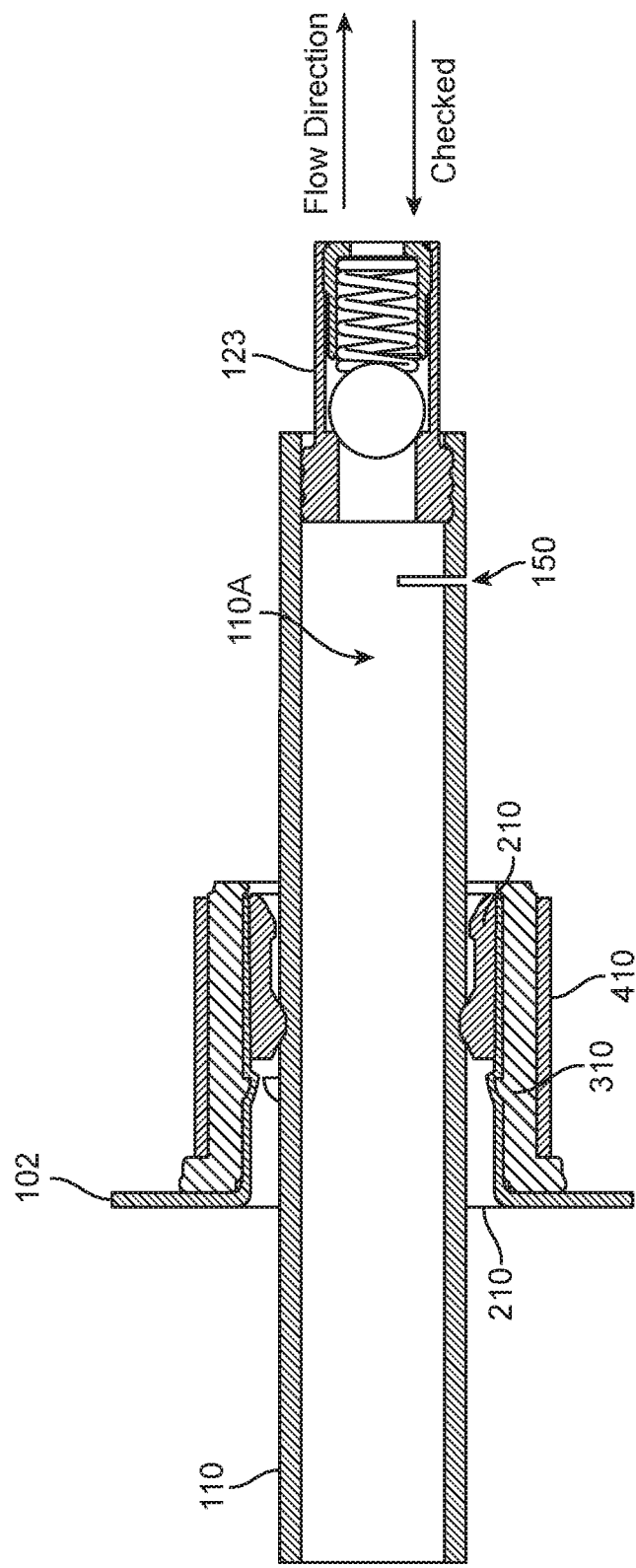
FIG. 10 illustrates an ASCA comprising a miniature check valve.

In some variations of the ASCA the functions of the plug and fill port(s) can be combined by using a micro-check valve 123. For example, both axial and side exit micro-check valves are available from The Lee Company, 2 Pettipaug Road, PO Box 424, Westbrook, Conn. 06498. See, for example, Lee part number CCPI25100xxS, where xx is the cracking pressure. In one of these variations the check valve may be installed in catheter balloon end 110A as a direct replacement for plug 120, as illustrated in FIG. 10, in which case the ASCA is similar to the variations described above, except there is no need for the catheter to comprise one or more fill ports. Instead, the fluid flows through the catheter and the (forward) pressure opens the check valve in the end of the catheter, allowing the fluid to enter reservoir. When the forward pressure stops, the check valve seals the end of the catheter. When the balloon is adequately filled the catheter is removed as previously described but the catheter balloon end is retained in the catheter jacket by the "plug" formed by the micro-check valve. As before, extractive forces above the design level cause the catheter to tear away at tear away slit 150.

Figure 11:
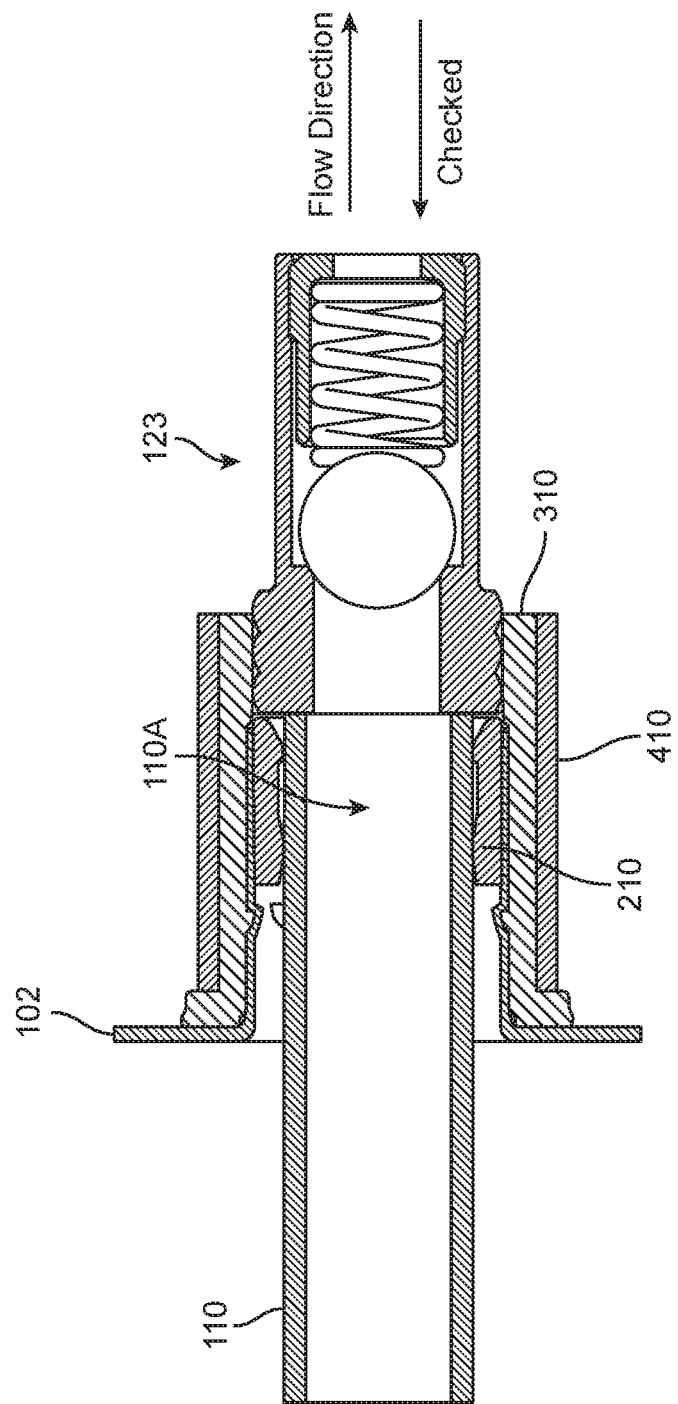
FIG. 11 illustrates a second variation of an ASCA comprising a miniature check valve.

An alternative variation, shown in FIG. 11, incorporates a micro-check valve 123 directly into the end of wall anchor 310 or retaining ring 410. In this latter variation the micro-check valve is part of the balloon device and the catheter is inserted into and held in catheter jacket 210 independently from the presence of a plug. By the design of catheter jacket 210, small withdrawal forces are inadequate to pull catheter 110 out of catheter jacket 210 but more significant withdrawal forces can pull the catheter from the catheter jacket. Such withdrawal can be accomplished with or without a tear slit.

What is claimed is:

1. A valve assembly for use with a balloon device having a fluid port, the valve assembly comprising:
   a jacket member having an elongated shape, an outer surface and an interior channel, the interior channel comprising an engagement member;
   a wall anchor positioned within the balloon device and adjacent to the fluid port, the wall anchor having an interior passage that receives the jacket member, where a portion of the balloon device adjacent to the fluid port extends into the interior passage of the wall anchor and is secured between the outer surface of the jacket member and the interior channel of the wall anchor;
   a conduit extending through the interior channel of the jacket member, the conduit having a fill end and a balloon end, wherein the conduit and the interior channel are configured to have a sliding resistance therebetween;
   the conduit having an interference region at the balloon end positioned within the balloon device, the interference region having a locking profile that allows the interference region to become fixedly engaged within the interior channel when moved therein;
   a weakened section located between the fill end of the conduit and the interference region, wherein the weakened section has a reduced tensile strength less than a tensile strength of the conduit while permitting sliding of the conduit relative to the interior channel upon the application of a pulling force on the conduit without causing separation at the weakened section, wherein the reduced tensile strength requires a tearing force to cause separation of the conduit at the weakened section; and
   a fill opening located on the conduit between the fill end and the interference region, the fill opening positioned within the balloon device such that fluid entering the fill end exits at the fill opening into the balloon, where the balloon end is occluded to prevent fluid from flowing therethrough, such that application of the pulling force that overcomes the sliding resistance causes movement the fill opening and the interference region into the jacket member to seal the balloon device.

2. The valve assembly of claim 1, where the jacket member comprises an elongated cylindrical shape.

3. The valve assembly of claim 1, where the balloon end of the conduit includes a cylindrical plug having an external shaft diameter equal to or greater than an interior diameter of the conduit.

4. The valve assembly of claim 3, where the cylindrical plug comprises a plug head sized to prevent movement through the interior channel of the conduit.

5. The valve assembly of claim 3, wherein the cylindrical plug comprises at least one tooth comprising a tapered shape that increases a force required to remove the plug from the conduit.

6. The valve assembly of claim 1, wherein the conduit includes a spherical plug in the balloon end of the conduit, where an external diameter of the spherical plug is equal to or greater than an interior diameter of the conduit.

7. The valve assembly of claim 1, wherein the interference region is adjacent to the balloon end.

8. The valve assembly of claim 1, wherein the weakened section is located between the fill end and the interference region.

9. The valve assembly of claim 1, where the interior channel of the jacket member includes at least one engaging element that reduces an interior diameter of the interior channel, wherein the interference region locks with the at least one engaging element to seal the interior channel of the jacket member.

10. The valve assembly of claim 1, wherein the wall anchor comprises a flared end adjacent to the balloon device.

11. The valve assembly of claim 1, where the conduit includes a plurality of fill openings.

12. The valve assembly of claim 1, wherein the portion of the balloon device extending into the interior passage of the wall anchor extends to at least a length of the jacket member.

13. The valve assembly of claim 1, wherein a proximal face of the wall anchor is adjacent to but unconnected with a wall of the balloon device.

14. The valve assembly of claim 1, wherein a friction fit between the conduit and the interior passage of the jacket member creates a resistance between the conduit and interior passage of the jacket member that permits movement of the balloon device upon pulling the conduit.

15. A balloon device comprising: a balloon layer defining a reservoir, the reservoir having a fluid port;
   a jacket member having an elongated shape, an outer surface and an interior channel, the interior channel comprising an engagement member;
   a wall anchor positioned within the balloon device and adjacent to the fluid port, the wall anchor having an interior passage that receives the jacket member, where a portion of the balloon device adjacent to the fluid port extends into the interior passage of the wall anchor and is secured between the outer surface of the jacket member and the interior channel of the wall anchor;
   a conduit extending through the interior channel of the jacket member, the conduit having a fill end and a balloon end, wherein the conduit and the interior channel are configured to have a sliding resistance therebetween;
   the conduit having an interference region at the balloon end positioned within the balloon device, the interference region having a locking profile that allows the interference region to become fixedly engaged within the interior channel when moved therein;
   a weakened section located between the fill end of the conduit and the interference region, wherein the weakened section has a reduced tensile strength less than a tensile strength of the conduit while permitting sliding of the conduit relative to the interior channel upon the application of a pulling force on the conduit without causing separation at the weakened section, wherein the reduced tensile strength requires a tearing force to cause separation of the conduit at the weakened section; and
   a fill opening located on the conduit between the fill end and the interference region, the fill opening positioned within the balloon device such that fluid entering the fill end exits at the fill opening into the balloon, where the balloon end is occluded to prevent fluid from flowing therethrough, such that application of the pulling force that overcomes the sliding resistance causes movement the fill opening and the interference region into the jacket member to seal the balloon device.

16. The balloon device of claim 15, where the jacket member comprises an elongated cylindrical shape.

17. The balloon device of claim 15, where the balloon end of the conduit includes a cylindrical plug having an external shaft diameter equal to or greater than an interior diameter of the conduit.

18. The balloon device of claim 17, where the cylindrical plug comprises a plug head sized to prevent movement through the interior channel of the conduit.

19. The balloon device of claim 17, wherein the cylindrical plug comprises at least one tooth comprising a tapered shape that increases a force required to remove the plug from the conduit.

20. The balloon device of claim 15, wherein the conduit includes a spherical plug in the balloon end of the conduit, where an external diameter of the spherical plug is equal to or greater than an interior diameter of the conduit.

21. The balloon device of claim 15, wherein the interference region is adjacent to the balloon end.

22. The balloon device of claim 15, wherein the weakened section is located between the fill end and the interference region.

23. The balloon device of claim 15, where the interior channel of the jacket member includes at least one engaging element that reduces an interior diameter of the interior channel, wherein the interference region locks with the at least one engaging element to seal the interior channel of the jacket member.

24. The balloon device of claim 15, wherein the wall anchor comprises a flared end adjacent to the balloon device.

25. The balloon device of claim 15, where the conduit includes a plurality of fill openings.

26. The balloon device of claim 15, wherein the portion of the balloon device extending into the interior passage of the wall anchor extends to at least a length of the jacket member.

27. The balloon device of claim 15, wherein a proximal face of the wall anchor is adjacent to but unconnected with a wall of the balloon device.

28. The balloon device of claim 15, wherein a friction fit between the conduit and the interior passage of the jacket member creates a resistance between the conduit and interior passage of the jacket member that permits movement of the balloon device upon pulling the conduit.

* * * * *

UNITED STATES PATENT AND TRADEMARK OFFICE
CERTIFICATE OF CORRECTION

Page 1 of 1

PATENT NO. : 10,470,908 B2
APPLICATION NO. : 16/286321
DATED : November 12, 2019
INVENTOR(S) : Nelson et al.

It is certified that error appears in the above-identified patent and that said Letters Patent is hereby corrected as shown below:

On the Title Page

Item (72), should read as follows: Inventors: David W. Nelson, Wayland, MA (US); Matthew J. Lapinski, Andover, MA (US); Bruce A. Horwitz, Newton, MA (US); Samuel Moss, Brookline, MA (US); Samuel Chadwick, Newton, MA (US)

Signed and Sealed this
Twenty-third Day of June, 2020

Andrei Iancu
*Director of the United States Patent and Trademark Office*